(12) United States Patent
Hien

(10) Patent No.: US 8,915,144 B2
(45) Date of Patent: Dec. 23, 2014

(54) METHOD FOR MEASURING A MATERIAL FLOW BY MEANS OF MICROWAVES, SENSOR MANAGEMENT AND DEVICE HAVING A SENSOR ARRANGEMENT

(75) Inventor: Peter Hien, Bad Muenstereifel (DE)

(73) Assignee: MSO Messtechnik und Ortung GmbH, Bad Münstereifel—Schönau (DE)

( * ) Notice: Subject to any disclaimer, the term of this patent is extended or adjusted under 35 U.S.C. 154(b) by 233 days.

(21) Appl. No.: 13/461,998

(22) Filed: May 2, 2012

(65) Prior Publication Data
US 2012/0279314 A1 Nov. 8, 2012

Related U.S. Application Data

(60) Provisional application No. 61/571,660, filed on Jul. 1, 2011, provisional application No. 61/586,297, filed on Jan. 13, 2012.

(30) Foreign Application Priority Data

May 2, 2011 (DE) .......................... 10 2011 100 244

(51) Int. Cl.
  *G01N 22/00* (2006.01)
  *A01C 7/10* (2006.01)
(52) U.S. Cl.
  CPC ...................................... *A01C 7/105* (2013.01)
  USPC ........................................... 73/861; 73/865.5
(58) Field of Classification Search
  None
  See application file for complete search history.

(56) References Cited

U.S. PATENT DOCUMENTS

| | | | |
|---|---|---|---|
| 2,824,284 A * | 2/1958 | Johnson | 342/104 |
| 3,881,353 A | 5/1975 | Fathauer | |
| 4,246,469 A | 1/1981 | Merlo | |
| 4,782,282 A | 11/1988 | Bachman | |
| 5,764,189 A * | 6/1998 | Lohninger | 343/700 MS |
| 6,768,317 B2 | 7/2004 | Möller et al. | |
| 2005/0140561 A1* | 6/2005 | Marsan et al. | 343/786 |
| 2010/0282114 A1* | 11/2010 | Reunamaki | 102/473 |

FOREIGN PATENT DOCUMENTS

| | | |
|---|---|---|
| DE | 25 12 494 | 11/1975 |
| DE | 101 00 664 | 7/2002 |
| DE | 101 12 499 | 9/2002 |
| DE | 203 05 448 | 8/2003 |
| DE | 102 36 515 | 9/2003 |
| DE | 10 2006 050 663 | 4/2008 |
| DE | 202 21 824 | 6/2008 |
| EP | 0 843 959 | 5/1998 |
| GB | 1003891 * | 9/1965 |
| WO | WO 99/40419 | 8/1999 |

* cited by examiner

*Primary Examiner* — Robert R Raevis
(74) *Attorney, Agent, or Firm* — Smartpat PLC; Axel Nix

(57) ABSTRACT

The invention relates to a method for measuring a material flow by means of microwaves, a sensor arrangement for measuring a material flow by means of microwaves and a device having a sensor arrangement, and to the use of a monostatic continuous wave radar for measuring a moving material flow consisting of particles or fluid. This has the advantage that the material flow consisting of particles or fluid can be quantitatively detected and/or the particles can be counted.

20 Claims, 3 Drawing Sheets

Figure 1:
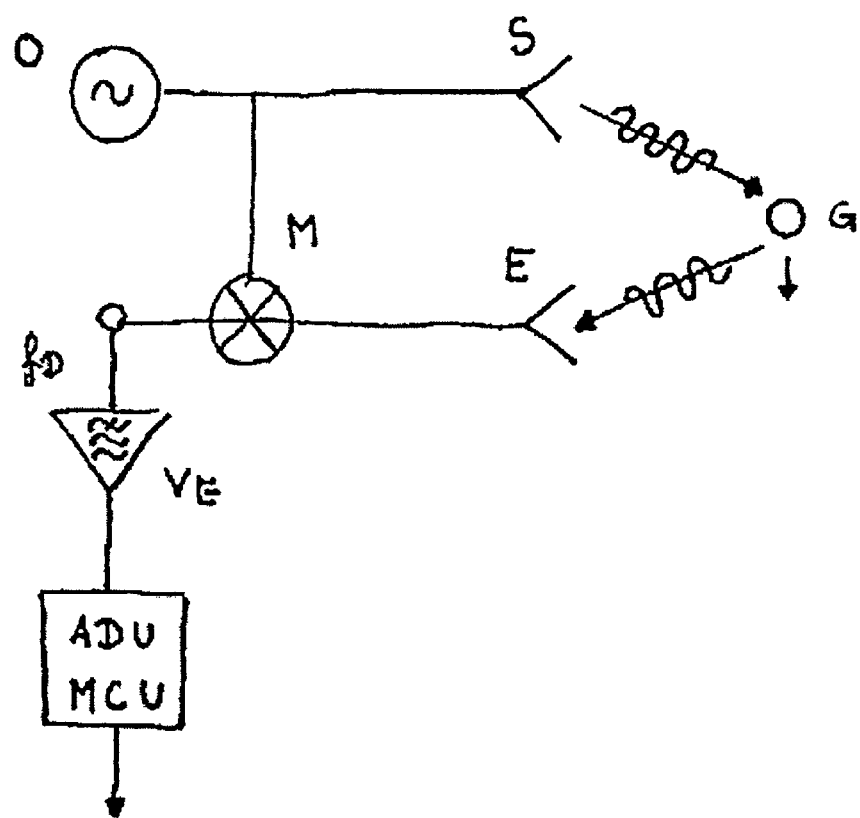

METHOD FOR MEASURING A MATERIAL FLOW BY MEANS OF MICROWAVES, SENSOR MANAGEMENT AND DEVICE HAVING A SENSOR ARRANGEMENT

CROSS REFERENCE TO RELATED APPLICATIONS

Applicant claims priority under 35 U.S.C. §119 of German Application No. 10 2011 100 244.1 filed on May 2, 2011, and under 35 U.S.C. §119(e) of U.S. Provisional Application Ser. No. 61/571,660 filed on Jul. 1, 2011, and 61/586,297 filed on Jan. 13, 2012, the disclosures of all of the above applications are incorporated herein by reference.

The invention relates to a method for measuring a material flow by means of microwaves, a sensor arrangement and a device having a sensor arrangement, and to the use of a monostatic continuous wave radar for measuring a flow of material which consists of particles or a fluid and which is moving.

In numerous industrial applications, material flows are pumped. The material which is fed can be particles, such as grains, granulates, pellets, coarse-grain powders etc. Example applications are the pneumatic or gravity-based feeding of grains, granulates, powders and pellets in e.g. agricultural sowing machines and pneumatic manure spreaders or centrifuging spreaders, in the food and animal feed industry, the building materials industry or in production, for example the feeding of plastic granulate to injection molding machines.

An application area from the prior art, which will be discussed in further detail below, is that of agricultural sowing machines. In single-grain sowing machines each seed coulter is associated with a metering unit, eg. for maize, beans, pilled sugar beet seeds or similar goods. In so-called drilling machines, by contrast, the seeds, e.g. cereals of all types, rape seed, grass seed or similar, are allocated from a container to a distribution system in proportion to the travelling speed by means of a metering unit. The seeds are fed in sequence through a plurality of pipes to the seed coulters either in free fall, the so-called mechanical sowing mechanism, or by means of an air stream, the so-called pneumatic sowing mechanism. In pneumatic drilling machines the seeds are blown into ball-segment shaped distribution heads from below from a metering unit via a main pipeline in the air stream. The material flow is distributed into sowing lines in the distribution head. The sowing line, the so-called seed pipe, feeds the seed to a particular seed coulter, which deposits the seed in the soil. A plurality of seed coulters is used in this process, e.g. with a seed coulter interval of 15 cm, corresponding to 60 seed coulters over a working width of 9 m. The metering of the seed takes place according to a calibration in proportion to the travelling speed, so that a particular distribution is obtained with regard to the mass or the number of seed grains per unit area. In evaluating the distribution, the longitudinal distribution, i.e. that in the direction of travel, is to be distinguished from the transverse distribution, i.e. the distribution across the working width of the machine.

A further application area is that of spreading machines ("centrifuging spreaders"). With these, granulated material is spread by centrifugal action, usually by a rotating disk, and so is distributed over an area.

Problematic aspects of the use of pneumatic sowing machines are:
the detection of a gradual or partial blockage or congestion in the pipe,
the measurement of the actual throughput, i.e. the mass and/or the number of grains per unit of time, and
the distributional accuracy in both the longitudinal and transverse distribution.

The prior art contains disclosures of numerous solutions for detecting a material flow. In sowing machines in particular the following sensors are known: optical sensors, which work reflectively or transflectively with one or more light detectors, e.g. a phototransistor, mechanical sensors such as a pin in the material flow with a piezo-element connected thereto for counting incident particles, mechanical vibration sensors for measuring the mechanical vibration due to the incidence of small bodies, the measurement of the impulse energy resulting from striking a piezo-element or an array of piezo-elements, radiometric sensors with a radiation transmission and scintillation detector, ultrasound sensors for measuring the energy reflected by the material flow and capacitive sensors as an amplitude-determining element in an oscillator circuit, as described for example in U.S. Pat. No. 4,782,282.

Also proposed has been the use of microwave absorption by the material flow, so-called TEM Transversal-Electromagnetic Mode, in the cavity resonator as described in U.S. Pat. No. 4,246,469.

Of these, the most frequently used in current practice are optical sensors for blockage detection and counting, usually of large seed grains, e.g. maize, soya beans, in single-grain sowing machines.

A problem in blockage detection is that this only addresses completely or extensively blocked pipes. If a blockade occurs in the seed coulter, then this is not detected until the pipe fills up with material up to the measuring point. Partial blockages with reduced throughput are difficult to detect.

Counting, i.e. detecting the throughput, is usually only possible with large seed grains, such as maize and soya beans. Counting the grains using optical sensors is error-prone, since double-counting can occur due to overlapping grains. A reliable optical count is technically very complex.

The object of the present invention is therefore to improve methods and sensor arrangements from the prior art.

According to a first aspect of the invention this object is achieved by a method for measuring a material flow consisting of particles or fluid by means of microwaves, in which a transmitted microwave signal and a received signal reflected from the material are superimposed and the resulting low-frequency beat signal is measured. The material to be sensed moves through the transmitted microwave signal. This signal is partially diffusely back-scattered and reflected by the material to be sensed. Due to the Doppler effect, the frequency of the reflected wave is shifted proportionally to the speed of the material. A mixing of the transmitted and the received signal causes the low-frequency beat signal, which is to be evaluated.

Advantageously, the amount of material flow, or the size of the particles is calculated from the amplitude of the beat signal. This is possible because the amplitude of the beat signal is proportional to the amount of material flow or the size of the particles.

In addition, from the frequency of the beat signal the speed of the material can be calculated. This is possible because the frequency of the beat signal is proportional to the speed of the material.

A further aspect of the invention relates to a sensor arrangement which is designed such that a method according to the invention can be carried out.

In the method, the sensor arrangement for measuring a material flow consisting of particles or fluid by means of microwaves with a microwave transmitter and a microwave receiver can be configured such that the transmitter and the receiver are arranged such that the microwaves are transmitted by the transmitter into a material flow and reflected by the material flow onto the receiver. The sensor arrangement of the microwave transmitter and microwave receiver continuously transmits electromagnetic waves. The material to be sensed moves through the emitted waves. The electromagnetic waves emitted by the transmitter are partially diffusely backscattered and reflected by the material to be sensed. The superposition causes the beat signal to occur at the receiver, which can then be analyzed in accordance with the method according to the invention.

It is advantageous if the transmitter emits microwaves with a frequency of 0.2 GHz to 600 GHz, in particular of 0.3 GHz to 300 GHz. The invention is also applicable to frequencies greater than 300 GHz.

Transmitter and receiver respectively transmit and receive electromagnetic waves by means of antennas. They can therefore comprise antennas. The antennas are advantageously implemented as planar or point-source radiator antennas with a main lobe of the emission characteristic covering the material flow.

Advantageously, the material flow can be moving in free fall, or thrown or flowing.

It is further advantageous if the sensor arrangement comprises a pipe for the material flow. Transmitter and receiver can then be mounted at an angle to the course of the pipe, so that electromagnetic waves can be continuously transmitted through the pipe from an antenna.

It is also possible to mount a plurality of sensor arrangements on one pipe. These can be arranged offset or above one another, for example. An arrangement at right angles is also conceivable. In this case the calculation of a cross-correlation is possible.

Each pipe can have a pneumatic feed for the material flow. In the case of pneumatic feeding the material is transported by means of compressed air. This is generated by compressing the surrounding air in a compressor. This allows the speed of the transported material to be determined. In addition, it is possible to transport the material against gravity.

Alternatively, the pipe can be inclined downwards. The seed can thus be transported by gravity.

Further advantage is gained if the pipe consists of a material which is transparent to the microwave signal. This can be, in particular, any non-metallic material. By means of the method and a sensor arrangement according to the invention, both a quantitative detection and a count of the particles of a moving material flow consisting of particles, so-called particulate material, in a pipework system is possible with high accuracy.

A third aspect of the invention comprises a device with a sensor arrangement according to the invention.

This device can be a sowing machine. In principle however, this aspect applies to all devices which relate to feeding a moving material flow consisting of particles or fluid. These can be e.g. grains, granulates, pellets or coarse-grain powders. As well as agricultural sowing machines and manure spreaders, it applies in particular to machines from the food and animal feed industry, the building materials industry or in production, in particular for transporting plastic granulate to injection molding machines.

If the device is a sowing machine, it is advantageous if it has a seeding tube which comprises a sensor arrangement. If multiple sensor arrangements are provided on multiple seeding tubes, then an exact monitoring and detection of the longitudinal and transverse distribution is possible.

Lastly, a final aspect of the invention comprises a use of a monostatic continuous wave radar for measuring a moving material flow consisting of particles or a fluid, wherein the particles or fluid are quantitatively detected and/or counted.

The continuous wave radar can be frequency-modulated or amplitude-modulated. Use of a pulsed radar is also possible.

In summary, the inventive idea of the present application has the following advantages:

The high-resolution measurement facilitates the detection of the amount of throughput and the counting of particles. Measurement at all seeding tubes of a sowing machine facilitates an exact monitoring and detection of the longitudinal and transverse distribution. Detection of a partial blockage with reduction of the throughput at individual seeding tubes is possible without first requiring a complete filling of the seeding tube up to the measuring point due to the blockage. In addition, detection and monitoring of the cessation of the seed flow is possible in individual pipes when laying down tramlines. In summary, the ability to measure the throughput in individual pipes therefore opens up potential for optimization by detection of blockages at an early stage and the monitoring, control and regulation of the longitudinal and transverse distribution.

In addition, the ability to count the individual grains substantially simplifies the calibration and adjustment of the sowing machine. A calibration procedure involving weighing becomes unnecessary.

Detection of duplications and multiple counting due to overlapping grains is possible by consideration of the signal amplitude.

By configuring the device as a sensor arrangement a simple mounting and retrofitting on existing machines is conceivable, without constructional modifications. No modifications are necessary, since nothing is installed in the feed path. Rather, the sensor arrangement is mounted from the outside, in contact with the existing pipe.

In contrast to optical sensors the proposed arrangement is insensitive to contamination. It is comparatively simple in its construction and inexpensive to produce.

The invention will now be described in more detail using an exemplary embodiment and with reference to the drawings.

Figure 2:
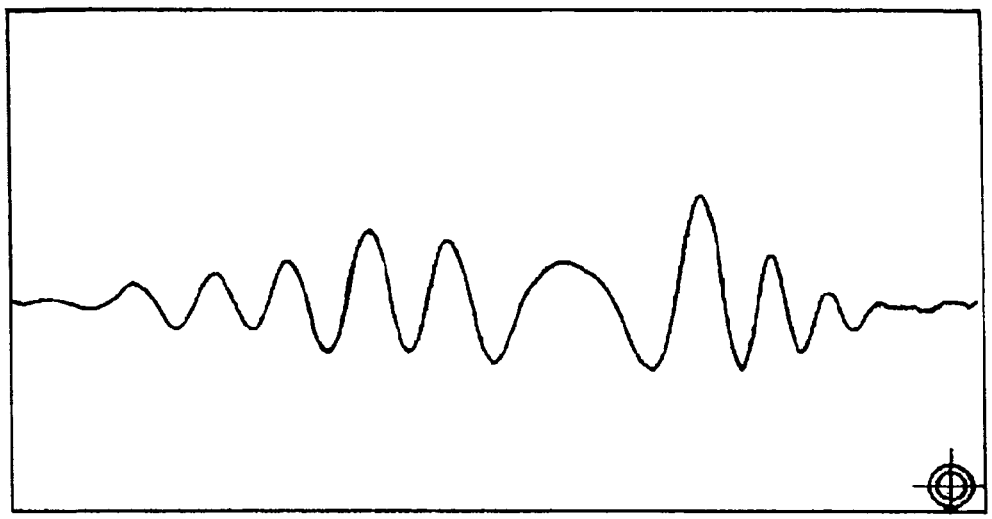
Figure 3:
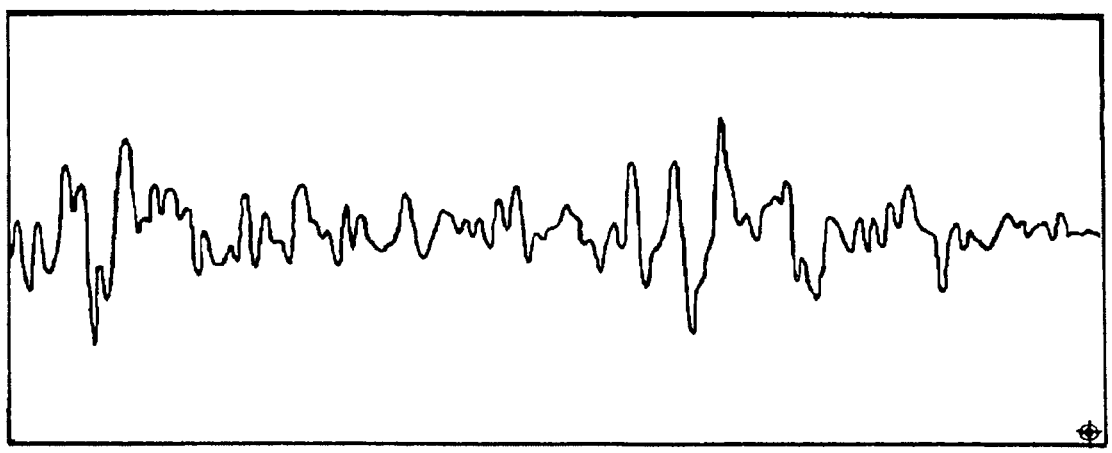
Figure 4:
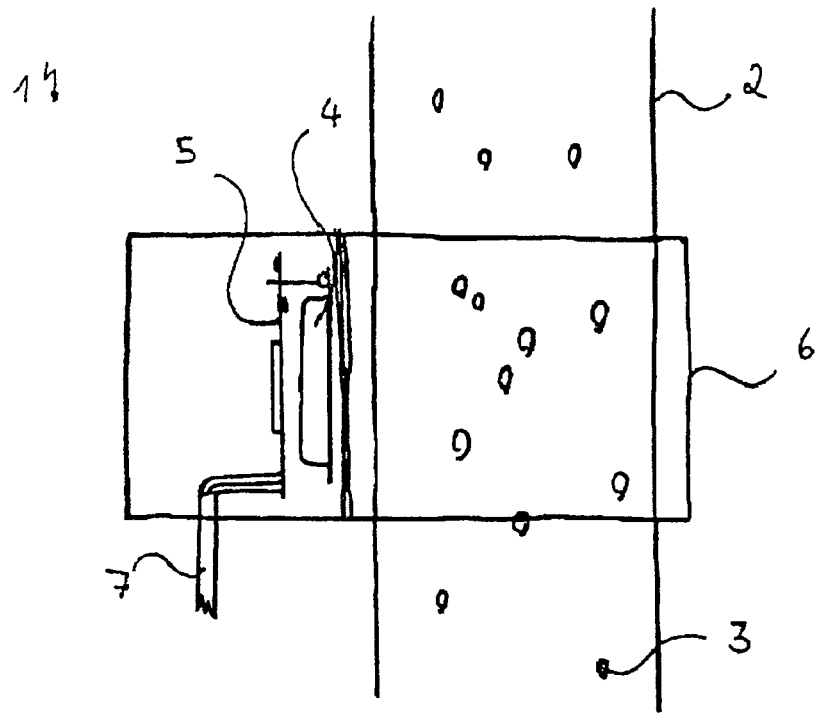
Figure 5:
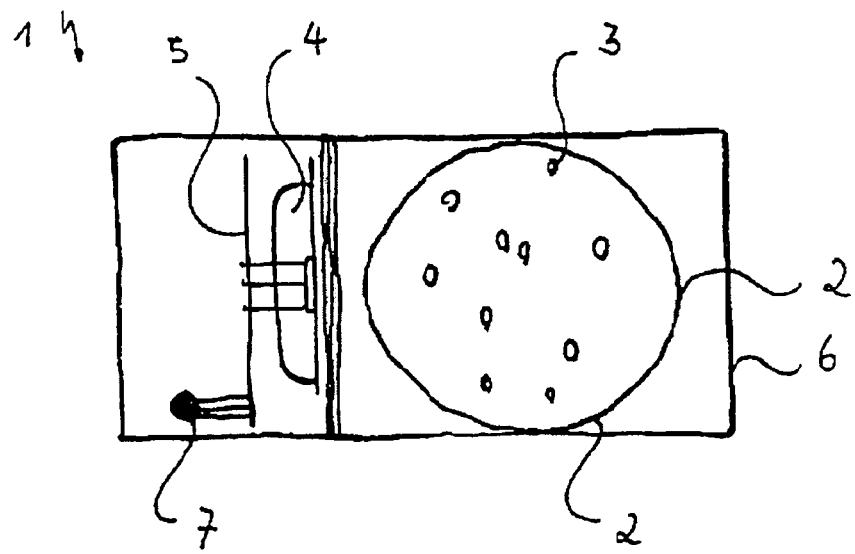

They show:

FIG. 1 a schematic sketch of a circuit for a sensor arrangement,

FIG. 2 a Doppler signal of a single grain, recorded in free fall through a pipe in front of the radar front end, FIG. 3 a Doppler signal of a granular material flow, FIG. 4 a schematic illustration of a sensor arrangement with a pipe in a side view, and FIG. 5 a schematic illustration of a sensor arrangement with a pipe in a plan view.

As can be identified on the schematic sketch in FIG. 1, the microwave signal generated by the oscillator O is transmitted via the transmitter to the material G. A portion of this signal is reflected onto the receiving antenna E. By means of a mixer M, the two signals are superimposed. This produces the Doppler frequency signal $f_D$, which is amplified by an amplifier or filter VE. After processing in an analog-digital converter ADU and a microcontroller MCU, the result is output.

FIGS. 2 and 3 show examples of such a Doppler signal $f_D$.

The sensor arrangement 1 illustrated in FIG. 4 and FIG. 5 is connected to a tube 2. A material flow with individual grains 3 is fed in the tube 2. The sensor arrangement with a radar front-end 4, which is connected to an electronic circuit 5 on a circuit board, is arranged in a metal housing 6. A cable 7 forwards the measurement results from the radar front-end 4, which have been processed by the electronics 5.

The invention claimed is:

1. A method for measuring a material flow through a pipe, the material in the material flow consisting of particles simultaneously flowing through the pipe or of a fluid, comprising:
   transmitting a microwave signal through a pipe wall into the material flow;
   receiving a reflected microwave signal from the material flow;
   superimposing the transmitted microwave signal and the reflected microwave signal to result in a low-frequency beat signal; and
   measuring the low-frequency beat signal.

2. The method according to claim 1, wherein the amount of material flow, or the size of the particles, is calculated from the amplitude of the beat signal.

3. The method according to claim 1, wherein the speed of the material is calculated from the frequency of the beat signal.

4. A sensor arrangement which implements the method according to claim 1.

5. A sensor arrangement for measuring a material flow through a pipe, the material in the material flow consisting of particles simultaneously flowing through the pipe or of a fluid, comprising:
   a microwave transmitter for generating a transmitted microwave signal;
   a microwave receiver for receiving a reflected microwave signal; and
   a mixer for superimposing the transmitted microwave signal with the reflected microwave signal to generate a low frequency beat signal,
   wherein the pipe comprises a pipe wall made of a material which is transparent to microwave signals and
   wherein the microwave transmitter and the microwave receiver are arranged such that the transmitted microwave signal is directed through the pipe wall into the material flow and reflected by the material flow through the pipe wall onto the microwave receiver.

6. The sensor arrangement according to claim 5, wherein the microwave signal generated by the microwave transmitter has a frequency between 0.2 GHz to 600 GHz.

7. The sensor arrangement according to claim 5, wherein the microwave transmitter and the microwave receiver comprise antennas.

8. The sensor arrangement according to claim 7, wherein at least one of the antennas is a planar antenna.

9. The sensor arrangement according to claim 7, wherein at least one of the antennas is a point-source radiator with a main lobe of emission characteristic covering the material flow.

10. The sensor arrangement according to claim 5, wherein the material flow is moving in free fall, or is thrown or flowing.

11. The sensor arrangement according to claim 5, wherein said arrangement has a pneumatic feed for the material flow.

12. The sensor arrangement according to claim 5, wherein the pipe is inclined downwards.

13. A device comprising a sensor arrangement according to claim 5.

14. The device according to claim 13, wherein said device is a sowing machine.

15. The device according to claim 13, wherein the pipe is a seeding tube and wherein the material in the material flow consists of a plurality of seeds simultaneously flowing through the pipe.

16. The device according to claim 13,
   wherein the microwave transmitter is a monostatic continuous wave radar and
   wherein the material in the material flow consists of particles, and
   wherein said particles are quantitatively detected and/or counted.

17. The device according to claim 13,
   wherein the microwave transmitter is a monostatic continuous wave radar and
   wherein the material in the material flow is a fluid, and
   wherein said fluid is quantitatively detected.

18. The device according to claim 16, wherein the continuous wave radar is frequency-modulated or amplitude-modulated.

19. The device according to claim 13,
   wherein the microwave transmitter is of a pulsed radar and
   wherein the material in the material flow consists of particles, and
   wherein said particles are quantitatively detected and/or counted.

20. The device according to claim 13,
   wherein the microwave transmitter is a pulsed radar and
   wherein the material in the material flow is a fluid, and
   wherein said fluid is quantitatively detected.

* * * * *